United States Patent [19]

Szántay et al.

[11] Patent Number: 5,545,741
[45] Date of Patent: Aug. 13, 1996

[54] PROCESS FOR THE PREPARATION OF EPIBATIDINE

[75] Inventors: Csaba Szántay; Zsuzsanna B. Kardos; István Moldvai; Eszter T. Major; Csaba Szántay, Jr.; Attila Mándi; Gábor Blaskó; Gyula Simig; Györgyi Lax; Sándor Drabant; Tamas Szállási; Márton Fekete; Gábor Gigler, all of Budapest, Hungary

[73] Assignee: Egis Gyogyszergyar Rt., Budapeset, Hungary

[21] Appl. No.: 341,221

[22] Filed: Dec. 5, 1994

[30] Foreign Application Priority Data

Dec. 9, 1993 [HU] Hungary .................. 93 03505

[51] Int. Cl.⁶ .................................. C07D 401/04
[52] U.S. Cl. .................. 546/276.7; 546/15; 546/338; 546/335; 546/337
[58] Field of Search .............................. 546/272

[56] References Cited

U.S. PATENT DOCUMENTS

| | | | |
|---|---|---|---|
| 4,245,112 | 1/1981 | Ficini et al. | 560/181 |
| 4,503,053 | 3/1985 | Nedelec et al. | 514/239 |
| 4,845,126 | 7/1989 | Hidasi et al. | 514/521 |
| 5,296,494 | 3/1994 | Lavielle et al. | 514/343 |

OTHER PUBLICATIONS

Fletcher et al. J. Org. Chem, 1994, 59, pp. 1771–1778.

*Primary Examiner*—Jane Fan
*Attorney, Agent, or Firm*—Beveridge, DeGrandi, Weilacher & Young, L.L.P.

[57] ABSTRACT

The invention relates to a process for the preparation of racemic or optically active epibatidine of the Formula XIV

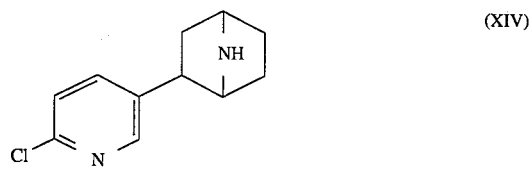

which comprises subjecting racemic or optically active epi-epibatidine-of the Formula XIII

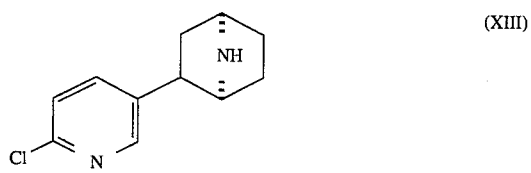

to epimerization in the presence base.

The advantage of the process is that readily available starting materials are used and the procedure is suitable for industrial scale productions too.

Epibatidine is a known highly affective analgesic active ingredient.

6 Claims, No Drawings

PROCESS FOR THE PREPARATION OF EPIBATIDINE

This invention relates to the preparation of an organic compound, namely epibatidin—2-(6-chloro-3-pyridyl)-7-azabicyclo[2.2.1]heptane—of formula (XIV).

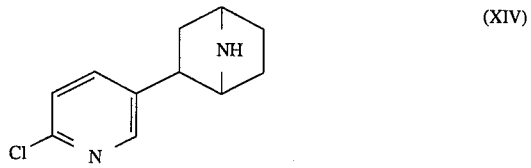

Epibatidine is a minor alkaloid isolated from the skin extracts of an Ecuadoran frog, Epipedobates tricolor, of the family Dendrobatidae. Considering the chemical structure it is the first natural substance containing a 7-azabicyclo[2.2.] -heptane skeleton. To the exo position of the said skeleton a 2-chloro-5-pyridyl substituent is attached, which can rarely be found in nature. The alkaloid possesses a valuable biological property, namely it has 200 times the analgesic potency of morphine. The mechanism of the analgesic effect is different from that of morphine, as it does not subside upon administering morphine antagonists (e.g. naxolone) (T. F. Spande, H. M. Garraffo, M. W. Edwards, H. J. C. Yeh, L. Pannell, J. W. Daly: J.Am. Chem. Soc., 1992, 114, 3475–3478).

Several processes have been disclosed in the literature for the syntehetic preparation of epibatidine:

1. Ch.A.Broka: Tetrahedron Letters, 1993 34, 3251–3254. In this reaction an adduct was prepared by the Diels-Alder reaction of enal obtained by the homologization of 6-chloronicotinic aldehyde and 2-(trimethylsilyloxy)-1,3-butadiene, it was then reduced with L-selectride, the hydroxy group of the product was protected by silylation, while the hydroxymethyl substituent was first converted into hydroxy group in 6 reaction steps and then benzoylated. By selective removal of the protecting groups the dihydroxy derivative was converted into 4-mesyloxycyclohexylamine containing a 6-chloropyridyl substituent, and the boiling of the latter compound in dichloromethane resulted in racemic epibatidine.

2. J. W. Daly, T. F. Spande, H. M. Garraffo: US Dept. Health and Human Service, U.S. Pat. No. 7,845,042-A. The key intermediate of this synthesis is 3-pyridyl-2-cyclohexa-1,3-diene, which was prepared from cyclohexane-1,2-dione and converted into Diels-Alder adduct with tert.butylnitrosoformiate. The adduct was hydrogenated catalytically, the thus-obtained aminoalcohol was treated with thionyl chloride, the product was cyclized and chlorinated by a photochemical reaction. The hydrolysis of the acid amide bond resulted in racemic epibatidine.

3. D. F. Huang, T. Y. Shen: Tetrahedron Letters, 1993, 34, 4477–4480. An adduct obtained by the Diels-Alder reaction of phenylsulfonyl-6-chloro-6-pyridylacetylene prepared from N-carbomethoxypyrrole and 6-chloronicotinic acid was desulfonated with sodium amalgam, hydrogenated catalytically, the protecting group was dehydrolized to obtain racemic epibatidine and racemic epi-epibatidine, which were then separated by column chromatography. The racemic epibatidine was resolved with di-p-toluyltartaric acid.

4. S. R. Fletcher, R. Baker, M. S. Chambers, S. C. Hobbs, P. J. Mitchell: J.Chem. Soc.Chem Comm., 1993, 1216–1218. The key intermediate of this synthesis route is tert.butyloxycarbonyl- 7-azabicyclo[2.2.] heptan-2-one, which was prepared in 7 reaction steps from cyclohexene amine containing a trifluoroacetyl protecting group and reacted with 5-lithio- 2-chloropyridine. From the thus-obtained adduct water was and the thus-formed double bound was hydrogenated catalytically to obtain a mixture of racemic epibatidine and epi-epibatidine isomers containing tert.butyloxycarbonyl protecting group. The undesired epimer was subjected to epimerization by boiling in tert.butanol in the presence of potassium tert.butylate. The racemic epibatidine was resolved by applying a chiral HPLC method and by salt formation with a chiral acid.

A serious drawback of the methods known from the literature resides in the cumbersome reaction steps which would make the industrial scale application rather complicated.

A further disadvantage of the known preparation methods resides in the fact that they require the application of difficultly available, expensive and inconvenient substances.

The invention aims at providing a method for the preparation of epibatidine, which is devoid of the drawbacks of the hitherto known processes and can be accomplished by using readily available and preparable substances even on an industrial scale. A further aim of the present invention is to provide an industrially applicable method for the preparation of epibatidine.

According to the present invention there is provided a process for the preparation of epibatidine of the Formula (XIV), which comprises a) subjecting racemic or optically active epi-epibatidine of the Formula XIII to epimerization in the presence of a base; or

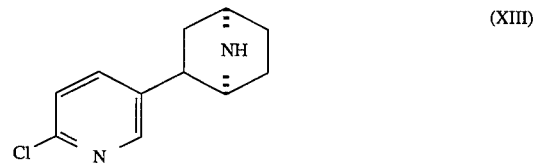

b) cyclising a racemic or optically active compound of the general formula I

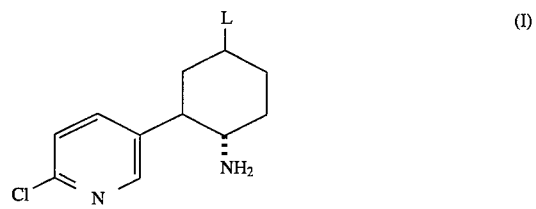

(wherein L stands for a leaving group) and thereafter subjecting the compound of the Formula XIII thus obtained to epimerization in the presence of a base; or c) selectively reducing the nitro group of a compound of the Formula IV;

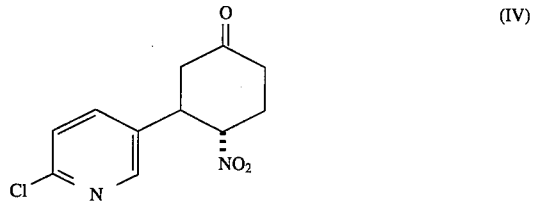

protecting the carbonyl group in the product thus obtained; diacylating the amino group of the compound of the Formula XV thus obtained;

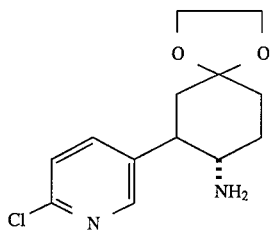

deprotecting the oxo group of the compound of the general Formula XVI

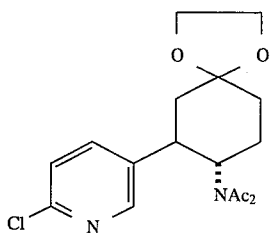

thus obtained (wherein Ac stands for an acyl group); exchanging in the compound of the general Formula XVII

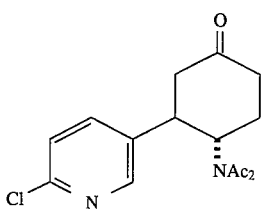

thus obtained (wherein Ac has the same meaning as stated above) the oxo group for an amino group; and cyclising the compound of the general Formula XVIII

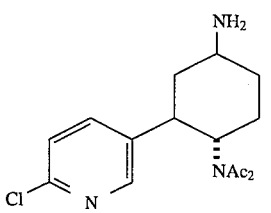

thus obtained (wherein Ac has the same meaning as stated above) into epibatidine of the Formula XIV; or d) cyclising the compound of the Formula V

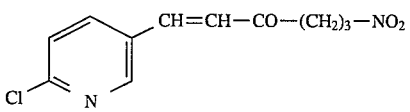

in the presence of an optically active base; and thereafter d$_1$) reducing the optically active compound of the Formula IV thus obtained;

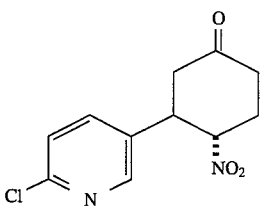

introducing into the optically active compound of the Formula III

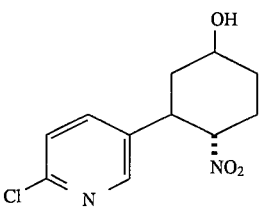

thus obtained an L leaving group; reducing the optically active compound of the general Formula II

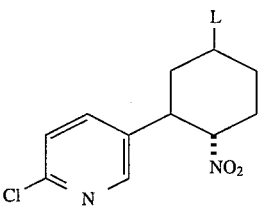

thus obtained (wherein L stands for a leaving group, preferably a lower alkylsulfonyloxy or arylsulfonyloxy group); cyclising the optically active compound of the general Formula I thus obtained (wherein L is as stated above); and subjecting the optically active compound of the Formula XIII thus obtained to epimerization in the presence of a base; or d$_2$) converting the optically active compound of the Formula IV into optically active epibatidine of the Formula XIV in accordance with process c); and if desired separating a racemic compound of the Formula XIV into the optically active isomers; or if desired separating a racemic intermediate product in any stage of the synthesis into the optically active isomers and converting the optically active isomer thus obtained into optically active epibatidine of the Formula XIV.

The epi-epibatidine of Formula XIII can be epimerized preferably under heating, preferably at the boiling point of the reaction mixture. The epimerization is carried out in the presence of a base. As base alkali alcoholates (e.g. potassium tert.butylate or sodium ethylate) or other organic alkali compounds(e.g. butyl lithium, lithium diisopropylamine etc.) can be applied. When using alkali alcoholates the epimerization is carried out under heating, in other cases it is performed at a temperature of about 0° C. It is preferable to carry out the reaction in an alcohol corresponding to the alkali alcoholate.

The compound of Formula XIV has a chiral structure, so it can be present in racemic of optically active form. The invention encompasses the preparation of both the racemic and the optically active compounds of formula XIV.

The racemic compound of formula XIV can optionally be resolved. The resolution can be carried out by methods known per se. One can proceed e.g. by reacting the racemate of the general formula XIV, with an optically active acid (such as tartaric acid,di-0,0'-p-toluyl-tartaric acid or dibenzoyltartaric acid), separating the thus-obtained diastereoisomeric salt pair (e.g. by fractional crystallization) and liberating the desired compound from the salt thereof.

The compound of Formula XIII can be prepared by subjecting a compound of the general Formula I to cyclization. In the general Formula I L represents a leaving group, preferably a lower alkylsulfonyloxy or arylsulfonyloxy group, particularly methanesulfonyloxy, p-toluenesulfonyloxy or p-bromophenylsulfonyloxy group. The particularly preferred starting compounds of the general Formula I contain methanesesulfonyloxy in the place of L. The ring closure is carried out under heating, preferably at the boiling point of the reaction mixture. The reaction is performed in an anhydrous aprotic solvent. For this purpose preferably halogenated hydrocarbons (such as methylene chloride, chloroform, chlorobenzene etc) or aromatic hydrocarbons (e.g. benzene, toluene, xylene) can be applied. The reaction is carried out under an inert gas atmosphere (e.g. under argon). The compound of Formula XIII thus obtained can be isolated from the reaction mixture by cooling the latter to room temperature, shaking it with an aqueous alkali hydroxide solution, separating the phases, extracting the aqueous phase with an appropriate organic Solvent (e.g. dichloromethane) and washing, drying and evaporating the combined organic phase. The thus-obtained compound of Formula XIII is-optionally purified by crystallization or column chromatography.

The compounds of the general Formula I can be prepared by reducing the compounds of the general Formula II. The reduction is carried out by catalytic hydrogenation or with the aid of chemical reducing agents.

When using chemical reducing agents the compounds of the general Formula II are preferably subjected to Bechamp reduction, or the reduction is performed with zinc in glacial acetic acid or with zinc, tin or iron in hydrochloric acid or with stannous(II) chloride. It is particularly preferable to carry out the reduction with stannous(II) chloride applying a polar organic solvent (e.g. lower alcohol or tetrahydrofurane). The chemical reduction can also be carried out in a neutral reaction medium.

When the reduction is carried out with stannous(II) chloride, preferably a polar solvent such as ethanol is applied as reaction medium. The reduction reaction with stannous(II) chloride can be carried out under heating, preferably at the boiling point of the reaction mixture. The thus obtained amino compound of the general Formula I can be isolated from the reaction mixture by cooling the mixture to room temperature and adding a water-immiscible solvent (e.g. a chlorinated hydrocarbon, preferably chloroform) to it and rendering the solution slightly alkaline. The separated precipitate is filtered off, washed with a water-immiscible solvent, the organic phases are combined, washed, dried and evaporated. The thus-obtained compound of the general Formula I is optionally purified by crystallization or column chromatography.

The starting substances of the general Formula II can be prepared as specified below. A particular advantage of the synthesis resides in the fact that 1-nitropentan-4-one of Formula X

$$NO_2-(CH_2)_3-CO-CH_3 \quad (X)$$

is used as starting substance, which can be obtained by reacting commercially readily available compounds, that is nitromethane of Formula XII

$$CH_3-NO_2 \quad (XII)$$

and methyl vinyl ketone of Formula XI.

$$CH_2=CH-CO-CH_3 \quad (XI)$$

The compound of the Formula X can be produced according to the method of D. E. Bergbreiter and J. J. Lalonde [J.Org. Chem./1987/, 52, 1601–1603].

In the next reaction step the compound of Formula X is brominated. The bromination is preferably carried out with elementary bromine in a lower alcohol (preferably methanol) at a temperature of about room temperature taking care of that the temperature of the reaction mixture should not rise above 40° C. The acetalic ether bond being formed in the reaction is hydrolized. The 1-bromo-5-nitropentan-2-one of Formula IX

$$NO_2-(CH_2)_3-CO-CH_2-Br \quad (IX)$$

is isolated by extracting the aqueous solution with a water-immiscible solvent (such as chlorinated hydrocarbons, aromatic hydrocarbons, ethyl acetate or —preferably—ether), washing the extract first acid-free with a caustic solution then neutral with water, dried and evaporated. The compound of the general Formula IX is optionally purified by column chromatography.

The compound of Formula IX is then reacted with a triarylphosphine to obtain a phosphonium salt of the general Formula VIII.

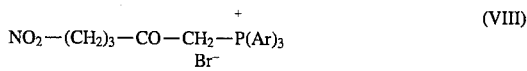
$$NO_2-(CH_2)_3-CO-CH_2-\overset{+}{P}(Ar)_3 \quad (VIII)$$
$$Br^-$$

In the latter formula Ar preferably stands for phenyl. The reaction is preferably carried out with triphenylphosphine in an apolar aprotic solvent (preferably in aromatic hydrocarbons, particularly in benzene). It is preferable to carry out the reaction by adding to the solution of the bromo compound of the general Formula IX in an apolar aprotic solvent a solution of triphenylphosphine composed with the same solvent. The reaction is carried out at a temperature between 10° C. and 30° C., preferably at room temperature. The oily product gets crystalline upon standing. The crystalline phosphonium salt of the general Formula VIII can be filtered off and washed.

The phosphonium salt of the general Formula VIII is then converted into a phosphorane of the general Formula VII. The phosphonium salt is dissolved in a water-immiscible apolar aprotic solvent (preferably in a halogenated aliphatic hydrocarbon, such as dichloromethane) and stirred with a diluted alkali hydroxide solution (e.g. sodium or potassium hydroxide solution) at a temperature of about room temperature. The phases are then separated, the organic layer is washed, dried and evaporated. In the Formula VII Ar is preferably phenyl.

The thus-obtained phosphorane of the general Formula VII

$$Ar_3P=CH-CO-(CH_2)_3-NO_2 \quad (VII)$$

is reacted with 6-chloropyridine-3-aldehyde (6-chloronicotinic aldehyde).of Formula VI.

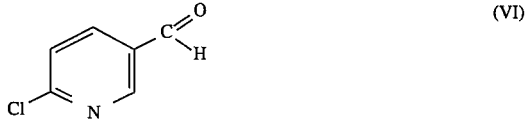

(VI)

The reaction can be performed in an anhydrous aprotic solvent (preferably in a halogenated aliphatic hydrocarbon, such as dichloromethane). The reaction can be carried out under heating, preferably at the boiling point of the reaction mixture. It is preferable to perform the reaction by adding to the solution of the phosphorane of the general Formula VII in an anhydrous aprotic solvent the solution of the aldehyde of the Formula VI composed with the same solvent. The reaction mixture is then cooled, washed and evaporated. The thus-obtained olefin of Formula V

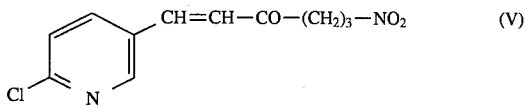

can be purified by crystallization or column chromatography.

The compound of Formula VI can be prepared readily from the commercially available 6-chloronicotinic acid by methods known from the literature [F. E. Ziegler, J. G. Sweeny: Tetrahedron Letters, (1969), 1097–1110].

The olefin obtained as specified above is then subjected to cyclization. This reaction is carried out in an anhydrous aprotic organic solvent. As reaction medium preferably cyclic ethers (e.g. tetrahydrofuran) can be applied. The cyclization is preferably carried out in the presence of a base, such as potassium fluoride applied onto a basic aluminium oxide carrier [D. E. Bergbreiter, J. J. Lalonde: J. Org. Chem. (1987), 52, 1601–1603]. The ring closure is carried out at a temperature of about room temperature. The thus-obtained nitroketone of Formula IV is isolated by removing the base and evaporating the solution. The thus-obtained compound of Formula IV can optionally be purified by crystallization or column chromatography.

The thus-obtained nitroketone of Formula IV is then reduced into the hydroxy compound of Formula III. The reduction is preferably carried out with complex metal hydrides. As reducing agent preferably sodium borohydride or L-selectride can be applied. The reduction with sodium borohydride proved to be particularly preferable. When sodium borohydride is applied as reducing agent the reduction is performed in a lower alcohol, preferably ethanol. One proceeds under tooling, preferably at a temperature of about 0° C. When the reaction has been accomplished the excess of the reducing agent is decomposed by the addition of a solvent containing an oxo group (such as acetone), the solvent is removed and the hydroxy compound of Formula III is isolated by dissolving the evaporation residue in a water-immiscible solvent (e.g. halogenated hydrocarbons, aromatic hydrocarbons, ether, ethyl acetate, preferably chloroform) and washing, drying and evaporating the organic phase. The compound of Formula III thus obtained is optionally purified by crystallization or chromatography.

The leaving group L is then introduced into the nitroalcohol of Formula III thus obtained to produce a compound of the general Formula II. The reaction is preferably carried out with the corresponding sulfonyl halide, preferably methanesulfonyl chloride. The acylating agent is preferably applied in excess. The reaction can be carried out in an apolar aprotic solvent (such as halogenated hydrocarbons, dichloromethane, pyridine) in the presence of a base (e.g. pyridine). It is preferable to perform the reaction in a mixture of dichloromethane and pyridine. The reaction can be carried out at a temperature of about room temperature. The compound of the general Formula II thus obtained can be isolated from the reaction mixture by removing the solvent, dissolving the residue in a water-immiscible organic solvent (e.g. halogenated hydrocarbons, aromatic hydrocarbons, ether, ethyl acetate, preferably chloroform), extracting the solution with an inorganic base (e.g. alkali carbonate), extracting the aqueous solution with the water-immiscible organic solvent which has been previously used, and washing, drying and evaporating the combined organic phases. The thus-obtained compound of the general Formula II can be optionally purified by crystallization or column chromatography.

According to process c) the nitro group of the compound of the Formula IV is selectively reduced under protecting the oxo group. Selective reduction may be carried out by catalytic hydrogenation or with the aid of chemical reducing agents. The oxo group may be preferably protected in the form of a ketale, particularly as ethylene ketale.

When a chemical reducing agent is used, the selective reduction of the compound of the Formula IV is preferably carried out by Bechamp reduction, or with zinc in glacial acetic acid, or with zinc, iron or tin in hydrogen chloride or with stannous (II) chloride. Reduction with stannous (II) chloride proved to be particularly advantageous. One may work preferably by using stannous (II) chloride in a polar organic solvent (e.g. a lower alkanol or tetrahydrofurane). Chemical reduction may be performed in neutral medium as well.

The selective reduction having been completed the reaction mixture is evaporated and the ketone group is protected preferably in the form of a ketale. This may be carried out by dissolving the evaporation residue in a water non-miscible apolar organic solvent (e.g. benzene or toluene, preferably benzene), adding a lower mono- or dihydric alcohol (e.g. methanol, ethanol, ethylene glycol or an ortho formic acid ester; preferably ethylene glycol) and heating the reaction mixture to boiling in the presence of an inorganic or organic acid, preferably pyridinium tosylate. The compound of the Formula XV thus obtained can be isolated in a known manner. Thus one may proceed by cooling the reaction mixture, separating the layers, making the benzene phase alkaline, washing with water and saturated brine, drying and evaporating. The ethylene glycol layer is made alkaline, the precipitated product is filtered, to the filtrate water is added and it is extracted with a water non-miscible organic solvent (e.g. a chlorinated hydrocarbon, preferably chloroform). The organic phase is washed, dried and evaporated. The evaporated residue thus obtained is combined with the evaporation residue of the benzene phase. The compound of the Formula XV thus obtained may be purified by column chromatography.

The compound of the Formula XV is subjected to diacylation of the amino group to yield a compound of the general Formula XVI. Thus a suitable leaving group is formed.

Diacylation may be carried out by dissolving the compound of the Formula XV in a polar aprotic solvent (e.g. dimethyl formamide) and reacting with an acylating agent in the presence of an organic base (e.g. triethyl amine, sodium hydride) at room temperature. It is preferred to use an acylating agent containing a sulfonyl group (e.g. p-toluene sulfonyl chloride, trifluoromethane sulfonyl chloride, methane sulfonyl chloride etc).

The compound of the general Formula XVI may be isolated from the reaction mixture by known methods. Thus one may proceed e.g. by pouring the reaction mixture into water, removing the precipitate by filtration, washing and drying. The compound of the general Formula XVI thus obtained may be purified by recrystallization or column chromatography if desired.

The compound of the general Formula XVII is prepared by deprotecting a compound of the general Formula XVI.

The protecting group of the oxo group may be removed by methods known per se. Thus the compound of the general Formula XVI may be dissolved in a lower organic solvent containing an oxo group (e.g. acetone) and heated to boiling in the presence of an organic or inorganic acid (preferably concentrated hydrochloric acid). One may proceed preferably by continuously distilling off acetone from the system and adding acetone dropwise to the reaction mixture at the same rate as acetone is removed.

The compound of the general Formula XVII may be isolated in a known manner. Thus one may proceed by cooling and evaporating the reaction mixture and adding a water non-miscible chlorinated hydrocarbon (e.g. chloroform) and a sodium hydroxide solution to the mixture. The layers are separated, the aqueous phase is extracted with chloroform, the united organic phases are washed, dried and evaporated. The compound of the general Formula XVII may be purified by crystallization or column chromatography if desired.

The compound of the general Formula XVII thus obtained may be converted into a compound of the general Formula XVIII by exchanging the oxo group for an amino group. This reaction may be performed by dissolving the compound of the general Formula XVII in an anhydrous lower alkanol (preferably methanol) and reducing with a complex metal hydride in the presence of ammonium acetate. As reducing agent preferably litium cyano borohydride or particularly sodium cyano borohydride may be used. The reaction may be preferably carried out at room temperature.

The compound of the general Formula XVIII may be isolated in a known manner. Thus one may proceed by decomposing the excess of the reducing agent by adding an organic solvent containing an oxo group (e.g. acetone), evaporating the reaction mixture, dissolving the residue in a water non-miscible organic solvent, and washing, drying and evaporating the organic phase. The compound of the general Formula XVIII thus obtained may be purified by crystallization or column chromatography if desired.

The compound of the general Formula XVIII may be converted into the desired compound of the Formula XIV by cyclisation. The reaction may be preferably carried out by heating in an organic solvent in the presence of sodium borohydride. One may proceed preferably by dissolving the compound of the general Formula XVIII in an anhydrous dipolar aprotic solvent (e.g. dimethyl formamide) and heating the mixture to boiling in the presence of sodium borohydride. The compound of the general Formula XIV may be isolated by methods known per se. Thus one may proceed by pouring the reaction mixture into water and separating the compound of the Formula XIV by filtration or extraction. The compound of the Formula XIV may be purified by crystallization or column chromatography if desired.

The optically active forms of the compound of the Formula XIV may be prepared by several methods.

According to process d) a compound of the Formula V is subjected to cyclisation in the presence of an optically active base to yield an optically active compound of the Formula IV. As optically active base preferably/+/-α-phenyl ethyl amine or /—-/-α-phenyl ethyl amine may be used. The reaction may be carried out in the presence of an inert organic solvent, preferably an ether (e.g. tetrahydrofurane or dioxane).

The optically active compound of the Formula IV may be converted into optically acitve epibatidine of the Formula XIV in an analogous manner to that disclosed above in connection with the preparation of racemic epibatidine.

The still achiral but prochiral compound of the Formula V is converted into an optically active compound of the Formula IV by means of an enantioselective synthesis. The optically active compound of the Formula IV can be transformed into a dextro or laevo rotating epibatidine of the Formula XIV with the aid of the synthesis steps described above for the preparation of racemic epibatidine.

Optically active epibatidine of the Formula XIV can also be prepared by separating racemic epibatidine of the Formula XIV into the optically active isomers or subjecting a racemic intermediate at a suitable stage of the synthesis to resolution and converting the optically active intermediate thus obtained into optically active epibatidine of the Formula XIV.

According to a preferred embodiment of the above process racemic epi-epibatidine of the Formula XIII is subjected to resolution. The process may be carried out by reacting racemic epi-epibatidine of the Formula XIII with an optically active acid (e.g. optically active tartaric acid, dibenzoyl tartaric acid or di-0,0'-p-toluyl tartaric acid), separating the diastereoisomeric salts thus formed (e.g. by fractionated crystallization) and setting free the optically active epi-epibatidine from the salt thereof.

According to a further embodiment of the process an other intermediate of chiral structure is subjected to resolution and the optically active intermediate thus obtained is converted into the desired optically active end-product in an analogous manner to the process described above for the preparation of racemic epibatidine of the Formula XIV. One may proceed preferably by subjecting the racemic nitro alcohol of the Formula III to resolution and carrying out further steps of the synthesis by using the optically active compound of the Formula III thus obtained. The racemate of the Formula III may be preferably separated into the optically active isomers by acylating the racemic compound with optically active menthyl chloro formiate (chloro formic acid menthyl ester), separating the diastereomers thus formed by crystallization and thereafter removing the menthyl group to yield the desired optically active compound of the Formula III.

Further details of the present invention are to be found in the Examples without limiting the scope of protection to these Examples.

EXAMPLE 1

1-bromo-5-nitro-pentane-2-one 80.0 g (0.61 mole) of 1-nitro-pentane-4-one are dissolved in 250 ml of anhydrous methanol, whereupon 31.5 ml (0.61 mole) of bromine are quickly added under cooling with ice. The reaction mixture is stirred for a further 2 hours at a rate that the internal temperature should not exceed 40° C. To the reaction mixture 250 ml of water are added, the reaction mixture is stirred at room temperature overnight. Next morning the solution is extracted three times with 300 ml of ether each, the etheral solution is washed with a 10 % sodium carbonate solution free of acid, whereupon it is washed three times with 200 ml of water each and 200 ml of a saturated sodium chloride solution, dried over calcium chloride and evaporated. The dry residue is subjected to chromatogaphy on a silica column and eluted with a 3:1 mixture of n-hexane and ethyl acetate. Thus 70.4 g of the desired compound are obtained in the form of a faint yellow liquid, yield 55%. $R_f$=0.30. $IR_{(film)}$:2950, 1720, 640 cm$^{-1}$.

EXAMPLE 2

(5-nitro-pentane-2-one)-triphenyl-phosphonium bromide 10.25 g (0.048 mole) of the bromine compound prepared according to Example 1 are dissolved in 30 ml of anhydrous benzene whereupon a solution of 14.09 g (0.0537 mole) of triphenyl phosphine and 50 ml of anhydrous benzene is added dropwise. The reaction mixture is stirred at room temperature for 48 hours whereby the oily precipitate becomes crystalline. The precipitated salt is filtered and washed with n-hexane. Thus 20.5 g of the desired compound are obtained, yield 89 % mp.: 70°–72° C.

EXAMPLE 3

(5-nitro-pentane-2-one)-triphenyl-phosphorane 8.1 g (0.0171 mole) of the phosphonium salt prepared according to Example 2 are dissolved in 160 ml of dichloro methane and the solution formed is stirred with 136 ml (0,0542 mole) of a 1% sodium hydroxide solution for 30 minutes. The two phases are separated, the dichloro methane layer is washed three times with 100 ml of water each and with 100 ml of a saturated sodium chloride solution, dried over calcium chloride and evaporated. The dry residue is thoroughly triturated with n-hexane. Thus 4.8 g of the desired compound are obtained, yield 72 %, mp.: 94°–97° C.

EXAMPLE 4

1-[3-(6-chloro-pyridyl)]-3-oxo-6-nitro-hexa-1-ene

To a solution of the 13.5 g (0.0344 mole) of the phosphorane prepared according to Example 3 and 70 ml of anhydrous dichloro methane a solution of 3.1 g (0,022 mole) of 6-chloro-pyridine-3-aldehyde in 70 ml of anhydrous dichloro methane is added. The reaction mixture is heated to boiling for 8 hours in argon atmosphere. The reaction mixture is cooled, the dichloro methane solution is washed subsequently three times with 150 ml of water each and 150 ml of a saturated sodium chloride solution, dried over calcium chloride and evaporated. The dry residue is subjected to chromatography on a silica column and eluted with a 1:1 mixture of n-hexane and ehtyl acetate. Thus 4.7 g of the pure desired compound are obtained, yield 84 %. Mp.: 97°–100° C. $R_f$=0.52. $IR_{(KBr)}$:1700,1680,1620,1580,1550, 1100cm$^{-1}$.

EXAMPLE 5

(±)-1α-nitro-2β-[3-(6-chloro-pyridyl)]-cyclohexane-4-one 1.6 g (0,0063 mole) of 1-[3- (6-chloro-pyridyl)]-3-oxo-6-nitro-hexa-1-ene are dissolved in 50 ml of anhydrous tetrahydrofurane whereupon 4.0 g (0.089 mole) of potassium fluoride precipitated on aluminium oxide are added. The reaction mixture is stirred at room temperature overnight. The solid product is filtered, washed with ethyl acetate. The united filtrates are dried over calcium chloride and evaporated. The residue is purified by chromatography on a silica column and elution with a 1:1 mixture of n-hexane and ethyl acetate. Thus 1.1 g of the pure desired product are obtained, yield 59 %. Mp.: 118°–121° C. Rf=0.38. $IR_{(KBr)}$:1710,1585,1550,1100 cm$^{-1}$.

EXAMPLE 6

(±)-1α-nitro-2β-[3-(6-chloro-pyridyl]-cyclohexane-4β-ol 2.8 g (0.0110 mole) of are dissolved in 200 ml of anhydrous ethanol whereupon 1.2 g (0.0317 mole) of sodium borohydride are added within a period of about one hour and a half in small portions. The excess of the reducing agent is decomposed by careful addition of acetone, the reaction mixture is evaporated in vacuo, the solid residue is dissolved in a mixture of 50 ml of water and 200 ml of chloroform, the mixture is thoroughly shaken and the layers are separated. The aqueous phase is extracted three times with 200 ml of chloroform each. The united organic layers are washed twice with 200 ml of water each and 100 ml of a saturated sodium chloride solution, dried over calcium chloride and evaporated. Thus 1.9 g of the desired compound are obtained, yield 67 %, mp.: 149°–153° C. $R_f$=0.42 (10:1 mixture of chloroform and methanol). $IR_{(film)}$: 3380, 1580, 1570, 1550, 1100, 1080 cm$^{-1}$.

EXAMPLE 7

(±)-1α-nitro-2β-[3-(6-chloro-pyridyl)]-4β-methanesulfonyloxy-cyclohexane 1.0 g (0.003896 mole) of (±)-1α-nitro-2β-[3-(6-chloropyridyl)]-cyclohexane-4β-ol are dissolved in a mixture of 15 ml of anhydrous dichloro methane and 30 ml of pyridine, whereupon 0.75 ml (0.0097 mole) of methanesulfonyl chloride is added dropwise under cooling with icecold water. The reaction mixture is stirred at room temperature overnight and thereafter the solvent is removed in vacuo. The dry residue is dissolved in a mixture of 50 ml of chloroform and 25 ml of a 10 % sodium carbonate solution, the mixture is thoroughly shaken, the phases are separated. The aqueous phase is extracted three times with 50 ml of chloroform each. The united organic layers are washed three times with 100 ml of water each and 100 ml of a saturated sodium chloride solution, dried over calcium chloride and evaporated. The dry residue is subjected to chromatography on a silica column and eluted with a 1:1 mixture of n-hexane and ethyl acetate. Thus 1.18 g of the desired compound are obtained, yield 91%, mp.: 120°–122° C. $R_f$=0.46. $IR_{(KBr)}$: 1590, 1570, 1540, 1530, 1450, 1350, 1180, 1090 cm$^{-1}$.

EXAMPLE 8

(±)-1α-amino-2β-[3-(6-chloro-pyridyl)]-4β-methanesulfonyloxy-cyclohexane 1.5 g (0.0048 mole) of (±)-1α-nitro-2β-[3-(6-chloro-pyridyl)]-4β-methanesulfonyloxy-cyclohexane are dissolved in 150 ml of ethanol whereupon 10.76 g (0.0477 mole) of stannous(II)chloride dihydrate are added. The reaction mixture is heated to boiling for 24 hours, whereupon it is cooled, 200 ml of chloroform are-added and the pH is adjusted to 9 by adding a concentrated ammonium hydroxide solution.

The precipitated product is filtered, washed with chloroform, the organic phase is washed twice with 200 ml water and once with a saturated sodium chloride solution, dried over magnesium sulfate and evaporated. Thus 1.1 g of the desired compound are obtained in the form of a colourless oil, yield 80%. $R_f$=0.69 (chloroform: methanol=10:1)

EXAMPLE 9

Epi-epibatidine 1.1 g (0. 0036 mole) of (±)-1α-amino-2β-[3-(6-chloropyridyl)]-4β-methanesulfonyloxy-cyclohexane are dissolved in 150 ml of anydrous toluene and the reaction mixture is heated to boiling under argon overnight. The reaction mixture is then cooled, 25 ml of a 5 % sodium hydroxyde solution are added, the phases are thoroughly shaken, the layers are separated. The aqueous phase is extracted ten times with 20 ml of dichloro methane each. The united organic layers are washed twice with 100 ml of water each and 100 ml of a saturated sodium chloride solution, dried over magnesium sulfate and evaporated. The residue is subjected to chromatography on a silica column and eluted with a 1:1 mixture of chloroform and methanol. Thus 350 mg of the desired compound are obtained, yield 46%, faint yellow oil. $R_f$=0.35. (1:1 mixture of chloroform and methanol).

$IR_{(film)}$: 3260, 3220, 1580, 1560, 1760, 1200, 1100 cm$^{-1}$.

EXAMPLE 10

Epibatidine 20 mg (0.09 mmole) of epi-epibatidine prepared according to Example 9 are boiled in 3 ml of anhydrous t-butanol in the presence of 100 mg of potassium tert-butylate for 30 hours. After evaporation the product purified by chromatography on a silica gel column (eluent: 1:1 mixture of benzene and methanol).

Yield: 10 mg (50%) $R_f$=0.25

EXAMPLE 11

(±)-1α-amino-2β-[3-(6-chloro-pyridyl)]-cyclohexane-4-one-ethylene ketale 2.54 g (0.01 mole) of (±)-1α-nitro-2β-[3-(6-chloro-pyridyl)]-cyclohexane- 4-one are dissolved in 250 ml of ethanol, whereupon 27.0 g (0.01 mole) of stannous(II)chloride dihydrate are added and the reaction mixture is heated to boiling for 24 hours. The solution is evaporated to dryness, whereupon to the residue 50 ml of ethylene glycol, 250 ml of benzene and 2.5 g of pyridinium tosylate are added. The reaction mixture is heated to boiling until no more water escapes (about 6 hours). The reaction mixture is cooled, the two layers are separated, the benzene and ethylene-glycol layers are separately made alkaline by adding a concentrated ammonium hydroxide solution (pH 9). The benzene phase is washed three times with 150 ml of saturated brine each and dried over magnesium sulfate. The ethylene glycol phase is filtered, the precipitate is thoroughly washed with chloroform. To the filtrate 300 ml of water are added, it is extracted five times with 200 ml of chloroform each, the united organic phases are washed twice with 300 ml of saturated brine each and dried over magnesium sulfate. The chloroform and benzene layers are united and evaporated. The residue is purified on a silica column by eluting with a 10:1 mixture of chloroform and methanol. Thus 1.79 g of the pure desired compouond are obtained in the form of a colourness foam, yield 67%, $R_f$=0.34.

EXAMPLE 12

(±)-1α-tosylamino-2β-[3-(6-chloro-pyridyl)]-cyclohexane-4-one- ethylene ketale 2.0 g (0.007442 mole) of (±)-1α-amino-2β-[3-(6-chloro-pyridyil)]-cyclohexane- 4-one-ethylene ketale are dissolved in 60 ml of anhydrous dimathyl formamide, whereupon 2.1 ml (0.01506 mole) of triethyl amine and 2.84 g (0.01488 mole) of p-toluenesulfonyl chloride are added. The reaction mixture is stirred at room temperature for an hour and poured into 500 ml of icecold water. The precipitated product is filtered, dried and recrystallized from ethanol. Thus 2.2 g of the desired compound are obtained, yield 69.9 %, mp.: 182°–184° C. $R_f$=0.36.

EXAMPLE 13

(±)-1α-ditosylamino-2β-[3-(6-chloro-pyridyl)]-cyclohexane- 4-one ethylene ketale 4.4 g (0.0104 mole) of (±)-1α-tosylamino-2β-[3-(6-chloropyridyl)] -cyclohexane-4-one-ethylene ketale are dissolved in 250 ml of anhydrous dimethyl formamide, whereupon 1.5 g (0.0312 mole) of sodium hydride are added in small portions. The reaction mixture is stirred at room temperature for an hour, 5.95 g (0.0312 mole) of p-toluenesulfonyl chloride are added and stirring is continued for 2 hours. The reaction mixture is poured into 2 liters of icecold water, the precipitated product is filtered, dried and the residue is purified on a silica column by eluting with a 1:1 mixture of n-hexane and ethyl acetate. Thus 4.6 g of the pure desired compound are obtained, yield 57 % mp : 210°–213° C., $R_f$=0.39.

EXAMPLE 14

(±)-1α-ditosylamino-2β-[3-(6-chloro-pyridyl)]-cyclohexane-4-one 4.0 g (0.006931 mole) of (+)-1α-ditosylamino-2β-[3-( 6-chloro-pyridyl)$_3$ -cyclohexane-4-one ethylene ketale are dissolved in 200 ml of acetone whereupon 10 ml of concentrated hydrocloric acid are added. The reaction mixture is heated to boiling for 4 hours at such a rate that the acetone distilled off is continuously replaced by adding dropwise fresh acetone. The reaction mixture is cooled, dissolved in 200 ml of chloroform and the pH is adjusted to 9 by adding a 10% sodium hydroxide solution. The two phases are thoroughly shaken together, the aqueous layer is extracted twice with 100 ml of chloroform each. The chloroform solution is washed twice with 200 ml of water each and once with 200 ml of saturated brine, dried over magnesium sulfate and evaporated. The dry residue is purified on a silica column with a 10:1 mixture of benzene and methanol. Thus 1.55 g of the pure desired compound are obtained in the form of a colourless foam, yield 42%, $R_f$=0.53.

EXAMPLE 15

(±)-4β-amino-1α-ditosylamino-2β-[3-(6-chloro-pyridyl)]-cyclohexane 200 mg (0.3751 millimole) of (±)-1α-ditosylamino-2β-[3-( 6-chloro-pyridyl]-cyclohexane-4-one are suspended in 30 ml of anhydrous methanol, whereupon.289 mg (3.751 millimoles) of ammonium acetate, 24 mg (0.3.751 millimole) of sodium cyano borohydride and 16 mg (0.3751 millimole) of lithium chloride are added. The reaction mixture is stirred at room temperature for 2 hours whereupon the excess of the reducing agent is decomposed by adding a few drops of acetone and the solution is then evaporated. The dry residue is dissolved in 20 ml of chloroform and 10 ml of water, the two phases are separated and the aqueous layer is extracted twice with 10 ml of chloroform each. The united organic solutions are washed once with 10 ml of water, and once with 10 ml of saturated brine, dried over magnesium sulfate and evaporated. The dry residue is purified on a silica column and eluted With a 5:1 mixture of chloroform and methanol. Thus 116 mg of the pure desired compound are obtained, yield 58 %, mp.: 158°–162° C. $R_f$=0.18.

EXAMPLE 16

(±)-epibatidine 100 mg (0.1872 millimole) of (±)-4β-amino-1α-ditosylamino- 2β-[3-(6-chloro-pyridyl)]-cyclohexane are dissolved in 10 ml of anhydrous dimethyl-formamide, whereupon 100 mg (2.64 millimoles) of sodium borohydride are added and the reaction mixture is heated to boiling for 3 hours. After cooling the solution is poured into 25 ml of water and extracted five times with 10 ml of chloroform each. The chloroform layer is washed twice with 20 ml of water each and once with 20 ml of saturated brine, dried over magnesium sulfate and evaporated. The dry residue is purified on a silica column with a 1:1 mixture of chloroform and methanol. Thus 15 mg of the pure desired compound are obtained, yield 38 %. The spectrum of the product corresponds to that of racemic epibatidine.

EXAMPLE 17

(−)-1α-nitro-2β-[3-(6-chloro-pyridyl)]-cyclohexane-4-one 5.0 g (0-01963 mole) of 1-[3-(6-chloro-pyridyl)]-3-oxo-6-nitro-hexa-l-ene are dissolved in 50 ml of anhydrous tetrahydrofurane, whereupon 12.6 ml (0.09815 mole) of (+)-α-phenyl ethylamine are added. The reaction mixture is allowed to stand at room temperature for 3 days, whereupon the solution is evaporated. The product is purified by subjecting the crude product to chromatography on a silica column and eluting first with a 10:1 mixture of benzene and methanol ($R_f$=0.381 and thereafter with a 1:1 mixture of n-hexane and ethyl acetate ($R_f$=0.42). The product is crystallized from ethanol. Thus 1.45 g of the pure desired compound are obtained, yield 29%, mp.: 149°–151° C., $(\alpha)_D^V$=–86.2° (c=2, chloroform).

EXAMPLE 18

(+)-1α-nitro-2β-[3-(6-chloro-pyridyl)]-cyclohexane-4β-ol

A) (–)-1α-nitro-2β-[3-(6-chloro-pyridyl)]-cyclohexane-4β-ol-carbonic acid menthyl ester 1.536 g (6 millimoles) of racemic 1α-nitro-2β-[3-(6-chloro-pyridyl)]-cyclohexane-4β-ol are dissolved in a mixture of 30 ml of anhydrous dichloro methane and 1.4 ml of pyridine at room temperature. To the solution 3.0 ml (14 millimoles) of (–)-menthyl-chloro-formiate (Aldrich 24,530-5) are added dropwise. The reaction mixture is stirred at room temperature for 6 hours, whereupon further 0.2 ml of the reactant is added. The reaction mixture is allowed to stand overnight and then evaporated to dryness in vacuo. The residue is dissolved in a mixture of 60 ml of chloroform and 5 ml of water. The pH of the aqueous layer is adjusted to 9 with a 5 % sodium hydrogen carbonate solution. The layers are separated, the chloroform solution is washed three times with 20 ml of water each, dried over sodium sulfate, Filtered and evaporated in vacuo. The residue is crystallized from 100 ml of methanol under clarification with charcoal. Thus 1.2 g of the desired compound are obtained in the form of white crystals; yield 45.8 %, mp.: 98°–100° C., $[\alpha]_D^{25}$=–56.0° (c=0.5, chloroform).

The product thus obtained is Further purified by column chromatography (Merck 9385 silicagel, water pump vacuo:eluent:benzol:ethyl acetate=19:1). The fractions containing the desired compound ace evaporated. Thus 630 mg of an oil are obtained which is crystallized from methanol. Thus 280 mg of the desired compound are obtained, mp.: 183°–184° C., $[\alpha]_D^{25}$=–36.7° (c=0.5 chloroform).

B) (+)-1α-nitro-2β-[3-(6chloro-pyridyl)]-cyclohexane-4B-ol 100 mg of the above crystalline substance $[\alpha]_D^{25}$=–36.7 (c:0.5 chloroform)] are dissolved in a mixture of 20 ml of 10% sulfuric acid and 20 ml of ethanol and the solution is heated to boiling for 24 hours, whereupon the ethanol is removed in vacuo. To the aqueous residue about 30 ml of benzene are added and the mixture is evaporated again to dryness in vacuo. This operation is carried out five or six times. The residue is suspended in chloroform and the pH is adjusted to a value of about 10 by adding a concentrated ammonium hydroxide solution. The layers are separated, the chloroform solution is washed with water, dried over sodium sulfate, filtered and evaporated in vacuo. The residue is purified by column chromatography (Merck 9385 silica-gel, water pump vacuo:eluent:chloroform=methanol=20:1). The fractions containing the desired compound are united and evaporated. The residue is crystallized from ether. Thus 32 mg of the desired compound are obtained, mp.: 190°–194° C., $[\alpha]_D^{25}$=+63.9° (c=0.5, chloroform).

EXAMPLE 19

(+)-epi-epibatidine and (+)-epi-epibatidine dihydrochloride 1.00 g (5 millimoles) of racemic epi-epibatidine are dissolved in 20 ml of hot acetone, whereupon a solution of 0.96 g (2.5 millimoles) of (–)-di-0,0'-P-toluoyl-L-tartaric acid formed with a mixture of 20 ml of acetone and 10 ml of water is added. The solution remains clear for some minutes but later the precipitation of crystals starts from the hot solution. The mixture is allowed to cool to room temperature and allowed to stand overnight in a refrigerator. Next morning the precipitated crystals are filtered, washed with a mixture of 5 ml of acetone and 1 ml of water and dried. Thus 1.053 g of the salt are obtained. Mp.: 188°–190° C., $[\alpha]_D^{25}$=–56.9° (c=0.5, methanol).

1.00 g of the above salt is dissolved in a hot mixture of 100 ml ethanol and 5 ml of water and the solution is allowed to stand at room temperature for a week-end. The precipitated crystals are filtered, washed with a mixture of 5 ml of ethanol and 0.5 ml of water and dried. Thus 341 mg of the salt are obtained, mp.: 200°–201° C., $[\alpha]_D^{25}$=–53.4° (c=0.5, methanol).

300 mg of the above salt are suspended in a mixture of 120 ml of chloroform and 8 ml of water at room temperature and, sufficient amount of a 1 molar sodium hydroxide solution (about 0.2–0.3 ml) is added to adjust the pH of the aqueous phase to 9–10. The layers are separated, the chloroform solution is washed twice with 8 ml of water each, dried over sodium sulfate, filtered and evaporated in vacuo. Thus 155 mg of an oily product are obtained, $[\alpha]_D^{25}$=±36.1. (c=0,5, methanol).

On epimerizating the product according to Example 10 epibatidine is obtained which is converted into the hydrochloride. The rotation of the salt $[[\alpha]_D^{252}$=+34.8° (c=0.36, methanol)] corresponds to the value $[[\alpha]_D^{25}$=+34.7° (c=0.56, methanol] disclosed in prior art [S. R. Fletscher et al, J. Chem. Soc. Chem. Column. 1216 (1993)].

(–)-epi-epibatidine

The first crystallization mother-lye obtained by the preparation of (+)-epi-epibatidine is evaporated to dryness in vacuo and the crystalline residue is made water-free by evaporation on a rotating evaporator from benzene several times. Thus 649 mg or the product are obtained, mp: 164°–176° C., $[\alpha]_D^{25}$=–64.8° (c=0.5, methanol).

200 mg of the above salt are suspended in a mixture of 80 ml of chloroform and 6 ml of water. The pH is adjusted to 9–10 by adding a 1 molar sodium hydroxide solution. The layers are separated, the chloroform solution is washed with water (about 10 ml), dried over sodium sulfate, filtered and evaporated to dryness. Thus 96 mg of an oily product are obtained, $[\alpha]_D^{25}$=–17.2° (c=0.5, methanol).

400 mg of the above salt $[[\alpha]_D^{25}$=–64.8° (c= 0.5, methanol)] are treated in a chloroform suspension with 400 mg of a sodium hydroxide solution. The reaction mixture is worked up. 160 mg of an oily product are obtained $[D]_D^{25}$= –17.2° (c=0.5, methanol).

The oily crude product thus obtained (160 mg, 0.76 millimoles) is dissolved in 3.2 ml of hot acetone, whereupon a solution of 153 mg (0.396 millimoles) of (+)-di-0,0'-p-toluoyl-D-tartaric acid, 3.2 ml of acetone and 0.6 ml of water is added. The reaction mixture is allowed to cool to room temperature, allowed to stand for a few hours, the precipitated crystals are filtered, washed with some drops of aqueous acetone and dried. Thus 269 mg of the salt ace obtained, mp.: 196°–198° C. $[\alpha]_D^{25}$=+63.4° (c: 0.5, methanol).

200 mg of the above salt are recrystallized from a mixture of 4.5 ml of ethanol and 0.5 ml of water. Thus 124 mg of the pure salt are obtained, mp.: 204°–205° C., $[\alpha]_D^{25}=+60.3°$, (c=0.5 methanol).

100 mg of the salt thus obtained are treated with sodium hydroxide in a manner known per se in a chloroform suspension. Thus 60 mg of an oily product are obtained, $[\alpha]_D^{25}=-40.3°$ (c=0.5, methanol).

What we claim is:

1. Process for the preparation of racemic or optically active epibatidine of the Formula XIV

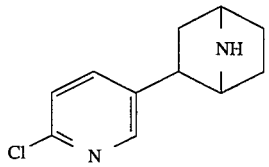

(XIV)

which comprises subjecting racemic or optically active epi-epibatidine of the Formula XIII

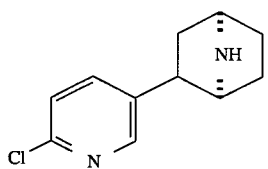

(XIII)

to epimerization in the presence of a base.

2. Process according to claim 1 which comprises carrying out epimerization at an elevated temperature.

3. Process according to claim 1 which comprises using an alkali alcoholate or an other organic alkali compound as base.

4. Process according to claim 3 which comprises using as base potassium tertiary butylate,, sodium ethylate or lithium diizopropyl amine.

5. Process according to claim 3 which comprises carrying out epimerization in the presence of an alkali alcoholate under heating, or in the presence of an other organic alkali compound at a temperature of about 0° C.

6. Process according to any of claim 2 which comprises carrying out the reaction in a lower alkanol as medium, in the presence of an alkali alcoholate corresponding to the alkanol used as solvent.

\* \* \* \* \*